United States Patent
Helland et al.

(10) Patent No.: US 6,760,622 B2
(45) Date of Patent: Jul. 6, 2004

(54) IMPLANTABLE MULTI-CHAMBER CARDIAC STIMULATION DEVICE WITH SENSING VECTORS

(75) Inventors: John R. Helland, Saugus, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 369 days.

(21) Appl. No.: 09/897,300

(22) Filed: Jul. 3, 2001

(65) Prior Publication Data

US 2003/0009197 A1 Jan. 9, 2003

(51) Int. Cl.[7] .................................................. A61N 1/18
(52) U.S. Cl. ........................................ 607/9; 600/512
(58) Field of Search .............................. 600/512; 607/9, 607/5

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,729,376 A | 3/1988 | DeCote, Jr. | 128/419 PT |
| 4,969,467 A | 11/1990 | Callaghan et al. | 128/419 PG |
| 5,101,833 A * | 4/1992 | Schmid | 600/512 |
| 5,350,410 A | 9/1994 | Kleks et al. | 607/28 |
| 5,466,254 A | 11/1995 | Helland | 607/123 |
| 5,514,161 A | 5/1996 | Limousin | 607/9 |
| 5,720,768 A | 2/1998 | Verboven-Nelissen | 607/9 |
| 5,738,105 A | 4/1998 | Kroll | 128/708 |
| 5,792,203 A | 8/1998 | Schroeppel | 607/30 |
| 5,800,465 A | 9/1998 | Thompson et al. | 607/9 |
| 5,902,324 A | 5/1999 | Thompson et al. | 607/9 |
| 6,081,748 A | 6/2000 | Struble et al. | 607/9 |
| 6,122,545 A | 9/2000 | Struble et al. | 607/9 |
| 6,430,435 B1 * | 8/2002 | Hsu et al. | 600/518 |

FOREIGN PATENT DOCUMENTS

| | | | |
|---|---|---|---|
| WO | WO 99/30777 | 6/1999 | A61N/1/368 |
| WO | WO 01/08748 A1 | 2/2001 | A61N/1/362 |

OTHER PUBLICATIONS

Cazeau, S., et al., "Four Chamber Pacing in Dilated Cardiomyopathy", PACE, vol. 17, Part II, pp: 1974–1979 (Nov. 1994).

* cited by examiner

*Primary Examiner*—Mark Bockelman

(57) ABSTRACT

An implantable multi-chamber cardiac stimulation device and method are provided for accurately sensing cardiac activity from three or four heart chambers using passive sensing electrodes placed in each heart chamber. Multiple intra-chamber or inter-chamber sensing vectors are established between passive sensing electrodes. Sampled sensing vector signals are processed such that a cardiac depolarization may be accurately detected, as well as its origin and direction of propagation. Time intervals between detected depolarization signals may be used to determine conduction time or heart rate. Diagnostic indicators of heart failure condition normally obtained from a 12-lead surface ECG study, such as P-wave or R-wave duration, may also be determined from the sensing vectors. Based on precise and detailed evaluation of sensing vector signals, stimulation therapy may be provided immediately upon a detected change in heart rhythm or heart failure condition.

40 Claims, 6 Drawing Sheets

IMPLANTABLE MULTI-CHAMBER CARDIAC STIMULATION DEVICE WITH SENSING VECTORS

FIELD OF THE INVENTION

The present invention relates generally to implantable cardiac stimulation devices, and in particular to multisite stimulation devices in which multiple sensing vectors are provided for accurate detection of cardiac events, their origin, and their conduction time and direction, by incorporating one or more passive sensing electrodes in each chamber of the heart.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A–V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart at a desired energy and rate. One or more heart chambers may be electrically stimulated depending on the location and severity of the conduction disorder.

Cardiac pacemakers conventionally stimulate a heart chamber by applying current pulses to cardiac tissues via two electrodes, a cathode and an anode. Standard pacing leads are available in either of two configurations, unipolar leads or bipolar leads, depending on the arrangement of the electrodes of a particular lead. A unipolar pacing lead contains a single electrode, normally the cathode, which extends pervenously distal from the pacemaker in an insulating enclosure until it is adjacent to the tip of the lead where the insulation is terminated to provide for electrical contact of the cathode with the heart tissue. The anode provides a return path for the pacing electrical circuit. For a unipolar lead, the anode is usually the pacemaker case.

A bipolar lead contains two electrodes within an insulating sheath, an anode that extends distal from the pacemaker to a position adjacent to, but spaced from, the electrode tip, and a cathode that also extends distal from the pacemaker, but terminates a short distance distal of the anode, at the lead tip. The anode commonly takes the form of a ring having greater surface area than the cathode tip. An insulating barrier separates the cathode and anode of a bipolar lead. In present-day pacemakers, circuits for pacing and sensing that determine tip, ring and case electrode connections are provided. Thus, the pacemakers can be programmed via telemetry for either bipolar or unipolar operation with respect to either sensing or pacing operations.

A single-chamber pacemaker delivers pacing pulses to one chamber of the heart, either one atrium or one ventricle, via either a unipolar or bipolar electrode. Single-chamber pacemakers can operate in either a triggered mode or a demand mode. In a triggered mode, a stimulation pulse is delivered to the desired heart chamber at the end of a defined time-out interval to cause depolarization of the heart tissue (myocardium) and its contraction. The stimulating pulse must be of sufficient energy to cause depolarization of the heart chamber, a condition known as "capture." The lowest stimulation output required to achieve capture is termed "threshold." The pacemaker also delivers a stimulation pulse in response to a sensed event arising from that chamber when operating in a triggered mode.

When operating in a demand mode, sensing and detection circuitry allow for the pacemaker to detect if an intrinsic cardiac depolarization, either an R-wave or a P-wave, has occurred within the defined time-out interval. If an intrinsic depolarization is not detected, a pacing pulse is delivered at the end of the time-out interval. However, if an intrinsic depolarization is detected, the pacing pulse output is inhibited to allow the natural heart rhythm to preside. The difference between a triggered and demand mode of operation is the response of the pacemaker to a detected native event.

Dual chamber pacemakers are now commonly available and can provide either trigger or demand type pacing in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g. the right atrium), and a separate unipolar or bipolar lead extends from a ventricular channel to the corresponding ventricle (e.g. the right ventricle). In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber.

If an intrinsic atrial depolarization signal (a P-wave) is not detected by the atrial channel, a stimulating pulse will be delivered to depolarize the atrium and cause contraction. Following either a detected P-wave or an atrial pacing pulse, the ventricular channel attempts to detect a depolarization signal in the ventricle, known as an R-wave. If no R-wave is detected within a defined atrial-ventricular interval (AV interval or AV delay), a stimulation pulse is delivered to the ventricle to cause ventricular contraction. In this way, rhythmic dual chamber pacing is achieved by coordinating the delivery of ventricular output in response to a sensed or paced atrial event.

Mounting clinical evidence supports the evolution of more complex cardiac stimulating devices capable of stimulating three or even all four heart chambers to stabilize arrhythmias or to re-synchronize heart chamber contractions. Reference is made to Cazeau et al., "Four Chamber Pacing in Dilated Cardiomyopathy," Pacing Clin. Electrophsyiol., 1994, 17 (11 Pt 2):1974–9. In order to achieve multi-chamber or multi-site stimulation in a clinical setting, conventional dual-chamber pacemakers have been used in conjunction with adapters that couple together two leads going to different pacing sites or heart chambers. Reference is made to U.S. Pat. No. 5,514,161 to Limousin.

In certain currently available devices for multi-chamber pacing, adapters are no longer required. The connection between leads is hardwired internally in the stimulation device connector block, coupling the ventricular leads to the ventricular channel and the atrial leads to the atrial channel.

While this design advantageously eliminates the need for adapters, the hardwire connections preclude the ability to distinguish between cardiac signals arising from a right chamber of the heart from cardiac signals arising from a left chamber of the heart. This obligatory coupling of the right and left heart chambers also prevents introducing separate timing between stimulation pulses delivered to the right and left chambers. Responding with a programmable delay between a sensed event in one chamber and delivery of an output pulse to the other chamber is thus made impossible.

Since one goal of multi-chamber stimulation is to provide a re-synchronization of the heart chambers in order to improve heart function in patients suffering from congestive heart failure, accurate detection of cardiac signals as well as recognizing the origin of a depolarization are important in achieving a desired therapeutic benefit from stimulation therapy. For example, it may be desirable to detect an intrinsic depolarization occurring in the right ventricle so that a stimulation pulse may be delivered to the left ventricle at a predefined time relative to the detected right ventricular depolarization in order to achieve optimal ventricular synchrony.

Traditionally, intrinsic cardiac events are detected by sensing the internal electrocardiogram (EGM) signals through conventional bipolar or unipolar sensing electrodes. Numerous problems can exist, however, in performing accurate cardiac event sensing. Various signals may be erroneously detected as a P-wave or an R-wave. Such signals include far-field signals (i.e., signals arising from the depolarization of another heart chamber), cross talk (i.e., signals arising from stimulation delivered in another heart chamber), premature atrial or ventricular depolarizations, depolarization of nearby skeletal muscle, or noise.

Erroneous detection or interpretation of the native cardiac rhythm will lead to inappropriate delivery or withholding of stimulation. Either of these results could have adverse effects on the patient's condition or even be life threatening. When sensing in three or all four chambers of the heart, the importance of accurate sensing and the possibility of erroneous sensing increase compared to less complicated dual chamber applications.

Relying on traditional unipolar or bipolar sensing in just the right atrium and the right ventricle, therefore, may not be adequate in multi-chamber stimulation devices. Discrimination between depolarization signals arising from the chamber being sensed and cross talk, noise or far-field signals becomes more complex when sensing and stimulating in three or even all four chambers of the heart.

During clinical assessment of patients, physicians frequently use 12-lead external ECG studies to monitor timing features of intrinsic cardiac signals in order to diagnose and monitor the progression of congestive heart failure. For example, the duration of the QRS signal shown an ECG is known to increase with worsening heart failure. A 12-lead ECG study can provide a physician with detailed information upon which the physician can base treatment decisions. However, in order to perform a 12-lead ECG study, the physician must be present and cannot practically monitor changes in the ECG signals continuously for the purposes of modulating treatment in response to improving or worsening heart condition. Therefore, it would be advantageous to obtain the kind of detailed information available from a 12-lead ECG study from internal EGM signals received by an implanted device. The device may then respond immediately in administering stimulation therapy such that the patient is receiving optimal therapy at all times.

There remains an unmet need for a multi-chamber cardiac stimulation device that allows accurate, reliable sensing of cardiac events and immediate stimulation therapy response. To this end, clear identification of the origin of a sensed event is needed as well as detailed timing information relating to specific cardiac events and diagnostic measures of changing heart condition. Therefore, a multi-chamber cardiac stimulation device capable of detailed sensing of events in all cardiac chambers is desirable.

SUMMARY OF THE INVENTION

The present invention addresses this need by providing a multi-chamber implantable cardiac stimulation device with associated leads and a method for accurate sensing of cardiac signals from all heart chambers including detection of the originating location of a cardiac signal. One or more passive sensing electrodes are provided on a lead placed in each heart chamber in addition to any desired stimulating electrodes. The passive sensing electrodes may be used for sensing a cardiac event within a heart chamber and are further used to create a set of sensing vectors for receiving multiple electromyogram signals from across cardiac chambers. Through processing of inter-chamber sensing vectors, for example subtracting or adding two or more inter-chamber signals, the origin of the detected events may be determined. Detailed information, such as QRS duration or P-wave duration as well as intervals between events, may also be gathered for monitoring changes in conduction or heart failure condition allowing the stimulation device to immediately administer stimulation therapy as necessary.

The foregoing and other features of the present invention are realized by providing an implantable cardiac stimulation device equipped with cardiac data acquisition capabilities. A preferred embodiment of the stimulation device includes a control system for controlling the operation of the device; a set of leads for delivering atrial and ventricular stimulation pulses and receiving cardiac signals through combinations of passive sensing electrodes that provide both intra-chamber and inter-chamber signals; a set of sensing circuits comprised of sense amplifiers for sensing and amplifying the cardiac signals; pulse generators for generating atrial and ventricular stimulation pulses; and a switching circuit for connecting desired electrode combinations to sensing circuits for sensing a set of EGM signals or to a pulse generator for stimulating in a desired heart chamber. In addition, the device includes memory for storing operational parameters for the control system. The device also includes a telemetry circuit for communicating with an external programmer.

In a preferred embodiment, a lead possessing one or more, preferably two, passive sensing electrodes in addition to electrodes used for pacing stimulation or shocking is placed in each heart chamber. Switching circuitry allows connection of multiple intra-chamber and inter-chamber combinations of the passive sensing electrodes to be connected to the sensing circuits. Digital processing of these signals, such as adding, subtracting, or other manipulation of digitized signals, is performed to remove undesired noise, far-field signals, or cross-talk. Further processing allows analysis of wavefront propagation through or across heart chambers, detailed analysis of signal durations and intervals between detected events, and determination of a signal origin. This information is used by the device control system for determining when and where stimulation therapy should be delivered.

The system and method of the present invention thus provide accurate sensing of cardiac signals in a multi-chamber stimulation device allowing for precise analysis of the timing and location of cardiac events and changes in cardiac function. This analysis improves device performance by allowing stimulation therapy to be delivered according to an accurate assessment of cardiac activity and function.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at providing precise evaluation of cardiac activity in a multi-chamber cardiac stimulation system using passive sensing electrodes for receiving multiple sensing vectors. A multi-chamber cardiac stimulation device will thus be described in conjunction with FIGS. 1 and 2, in which the sensing methods included in the present invention could be implemented. It is recognized, however, that numerous variations of such a device exist in which the methods presented herein could be implemented without deviating from the scope of the present invention.

Figure 1:
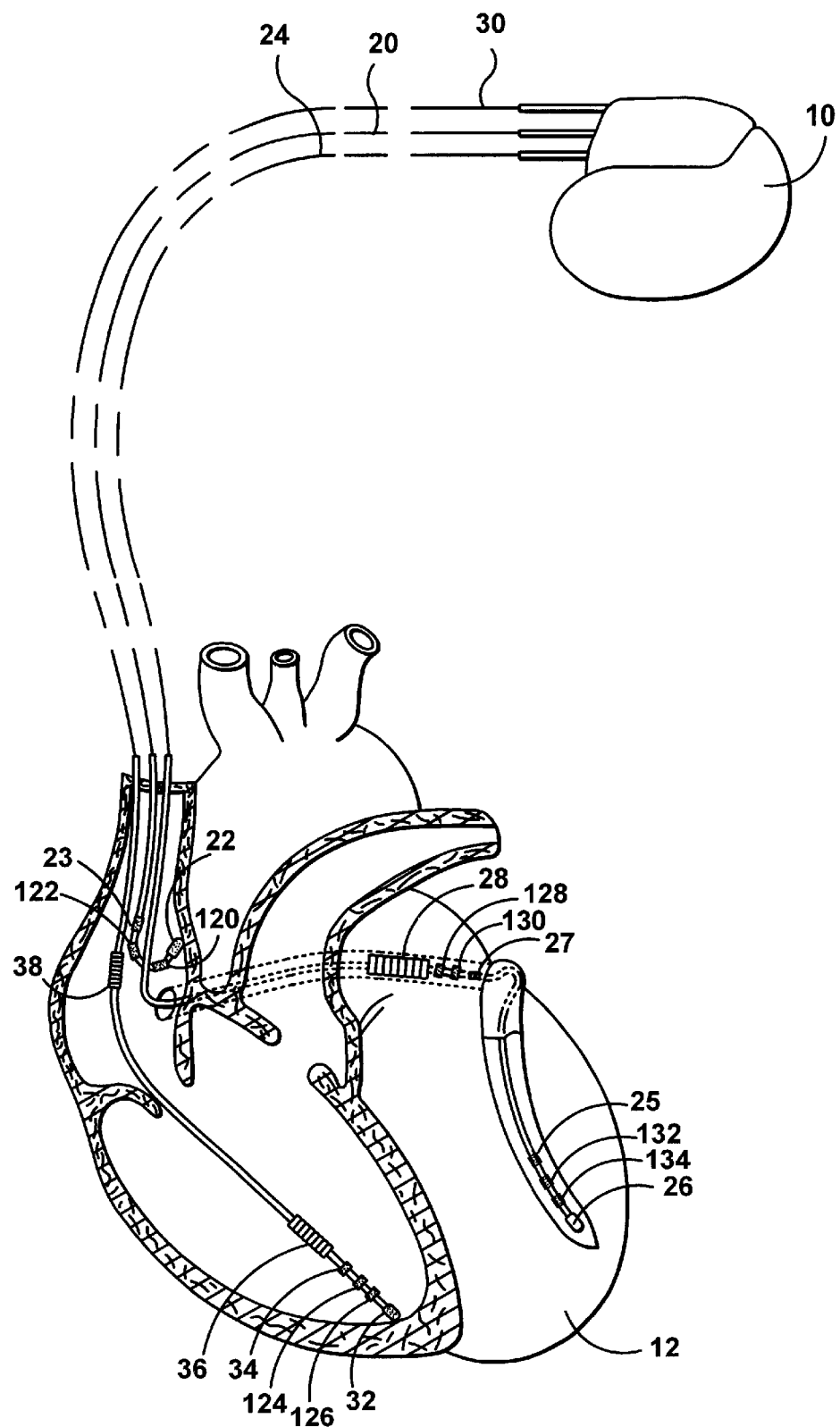
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

The right atrial lead 20 may also have an atrial ring electrode 23 to allow bipolar stimulation in combination with the atrial tip electrode 22. Right atrial lead 20 is further equipped with two right atrial passive sensing electrodes 120 and 122 for sensing right atrial signals or sensing inter-chamber signals when used in combination with sensing electrodes positioned in other heart chambers.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place distal electrodes adjacent to the left ventricle and additional electrodes adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to deliver left ventricular pacing therapy using at least a coronary sinus tip electrode 26 for unipolar stimulation or in combination with left ventricular ring electrode 25 for bipolar stimulation. Left atrial pacing therapy may be delivered using at least a coronary sinus ring electrode 27, and shocking therapy may be delivered using at least a coronary sinus coil electrode 28. For a more detailed description of a coronary sinus lead, refer to U.S. patent application Ser. No. 09/457,277, titled "A Self-Anchoring Coronary Sinus Lead" (Pianca et al.), and U.S. Pat. No. 5,466,254, titled "Coronary Sinus Lead with Atrial Sensing Capability" (Helland).

In accordance with one embodiment of the present invention, the coronary sinus lead 24 is further equipped with two left ventricular passive sensing electrodes 132 and 134 to be positioned adjacent the left ventricle and used for sensing left ventricular cardiac signals or sensing inter-chamber signals when used in combination with sensing electrodes positioned in other heart chambers. Two left atrial passive sensing electrodes 128 and 130 are also provided and positioned adjacent the left atrium for sensing left atrial signals or sensing inter-chamber signals when used in combination with sensing electrodes positioned in other heart chambers.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, a superior vena cava (SVC) coil electrode 38 and right ventricular passive sensing electrodes 124 and 126. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle. Passive sensing electrodes 124 and 126 are used to receive right ventricular signals or inter-chamber signals when used in combination with sensing electrodes positioned in other heart chambers.

Figure 2:
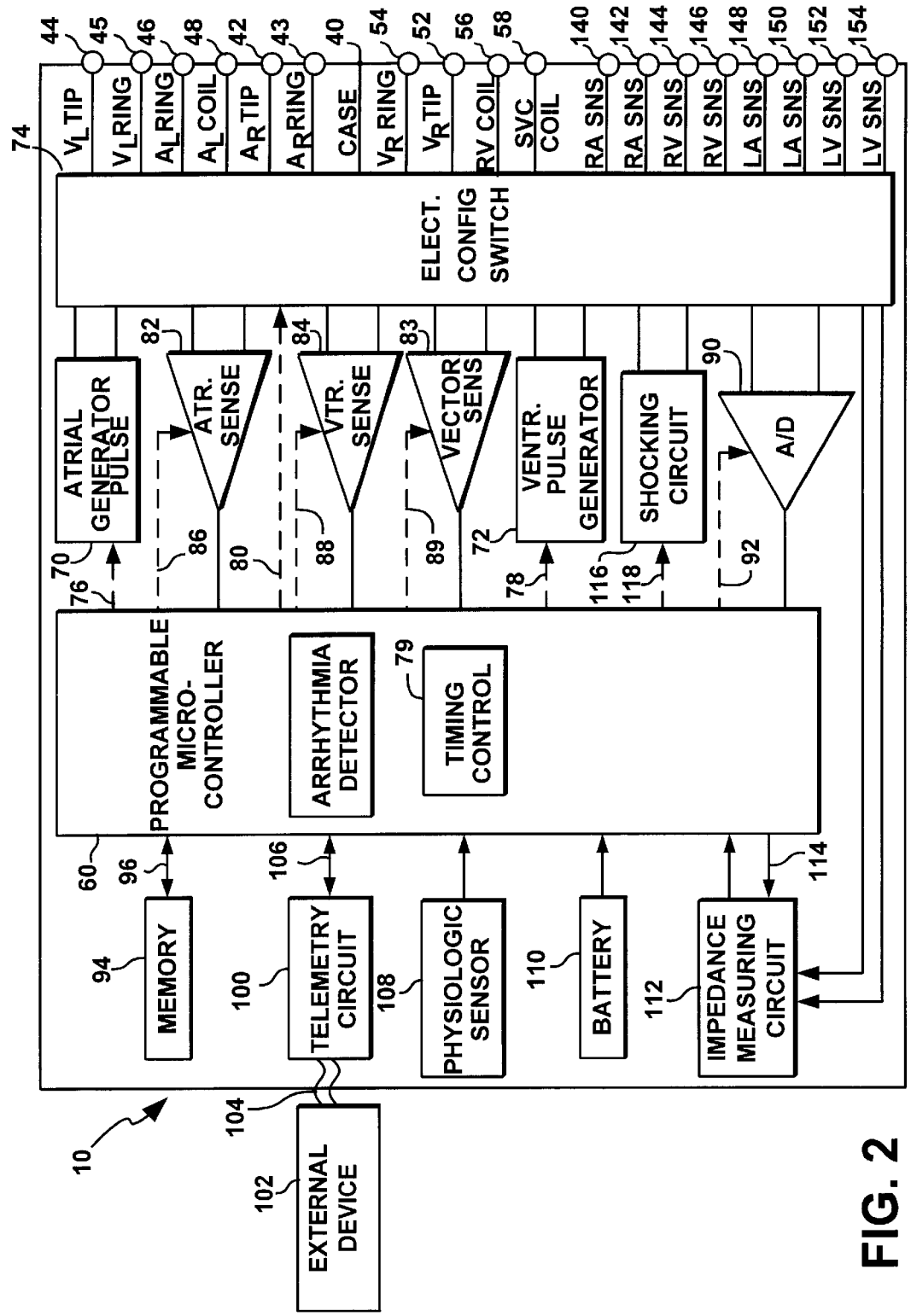
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The housing 40 further includes a connector having a plurality of terminals 42, 43, 44, 45, 46, 48, 52, 54, 56, 58, 140, 142, 144, 146, 148, 150, 152 and 154 (shown schematically and, for convenience, the names of the electrodes to which they are connected are shown next to the corresponding terminals). As such, to achieve right atrial stimulation, the connector includes at least a right atrial tip terminal ($A_R$ TIP) 42 adapted for connection to the atrial tip electrode 22. The connector may also include a right atrial ring terminal ($A_R$ RING) 43 for connection to the atrial ring electrode 23. Preferably, the connector further includes two right atrial passive sensing terminals (RA SNS) 140 and 142 for connection to the right atrial passive sensing electrodes 120 and 122 to achieve right atrial sensing and inter-chamber sensing vectors that include the right atrium.

To achieve left chamber pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the coronary sinus tip electrode 26, the left ventricular ring electrode 25, the coronary sinus ring electrode 27, and the coronary sinus coil electrode 28, respectively. To achieve left atrial sensing and inter-chamber sensing vectors that include the left atrium, the connector further includes two left atrial passive sensing terminals (LA SNS) 148 and 150 for connection to the left atrial passive sensing electrodes 128 and 130. To achieve left ventricular sensing and inter-chamber sensing vectors that include the left ventricle, the connector further includes two left ventricular sensing terminals (LV SNS) 152 and 154 for connection the left ventricular passive sensing electrodes 132 and 134.

To support right ventricular pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively. To achieve right ventricular sensing and inter-chamber sensing vectors that include the right ventricle, the connector further includes two right ventricular passive sensing terminals (RV SNS) 144 and 146 for connection to the right ventricular passive sensing electrodes 124 and 126.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, inter-chamber, etc.) by selectively closing the appropriate combination of switches.

Atrial signals are generally received by atrial sensing circuits 82 for the detection of events sensed in the atria. Ventricular signals are generally received by ventricular sensing circuits 83 for the detection of events sensed in the ventricles. The present invention further includes vector sensing circuits 83 for receiving inter-chamber sensing signals. Atrial sensing circuits 82, ventricular sensing circuits 84 and vector sensing circuits 83 may also be selectively coupled to the right atrial lead 20, coronary sinus lead 24, and the right ventricular lead 30, through the switch 74, for detecting the presence of cardiac activity in each of the four chambers of the heart. Accordingly, the atrial, ventricular and vector sensing circuits 82, 84, and 83 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity. As will be described in greater detail in conjunction with FIGS. 3 and 4, the switch 74 selectively connects the passive sensing electrodes 120, 122, 124, 126, 128, 130, 132, and 134 such that a desired set of inter-chamber sensing vectors as well as intra-chamber signals may be sensed.

Each of the atrial sensing circuit 82, the ventricular sensing circuit 84 or the vector sensing circuit 83 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial, ventricular and vector sensing circuits 82, 84 and 83.

For arrhythmia detection, the stimulation device 10 utilizes the atrial, ventricular and vector sensing circuits 82, 84, and 83 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". When automatic capture is enabled, the microcontroller 60 searches for a depolarization signal following a stimulation pulse during a "detection window" set by timing control circuitry 79 within microcontroller 60. The microcontroller 60 enables the data acquisition system 90 via control signal 92 to sample the cardiac signal that falls in the capture detection window. The sampled signal is evaluated to determine if it is an evoked response signal based on its amplitude, peak slope, or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

The implementation of capture detection circuitry and algorithms are described, for example, in U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.).

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by means of a control signal 114.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the coronary sinus coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the coronary sinus coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
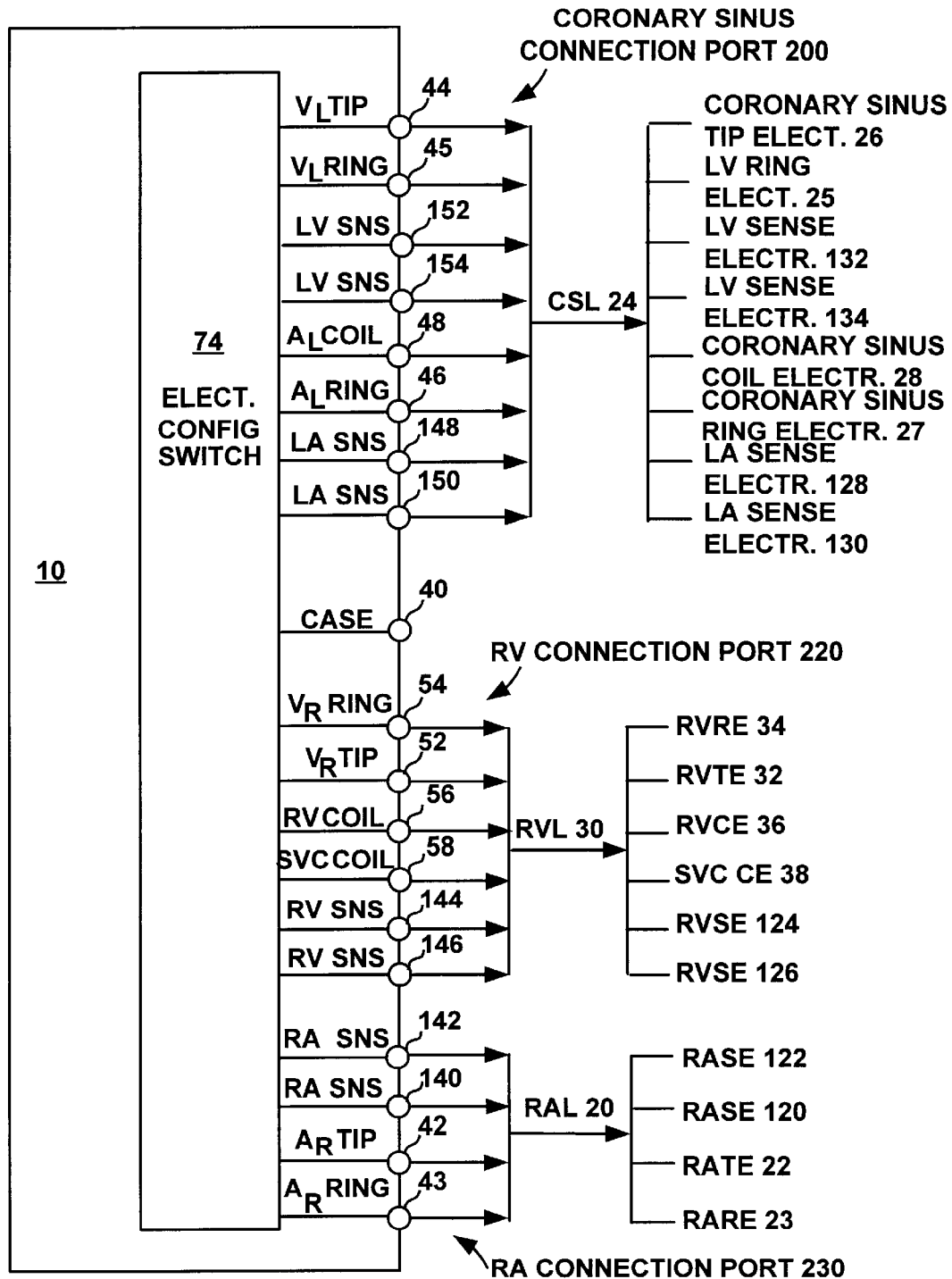
FIG. 3 is block diagram of the stimulation device of FIG. 2, illustrating a switch with three ports for connection to three multipolar leads possessing passive sensing electrodes and stimulating electrodes.

The stimulation device 10 of FIG. 2 includes three multipolar connection ports 200, 220 and 230 that are illustrated in FIG. 3. A coronary sinus connection port 200 accommodates the coronary sinus lead (CSL) 24 with terminals 44, 45, 46 and 48 that are associated with the coronary sinus tip electrode (CSTE) 26, the left ventricular ring electrode (LVRE) 25, the coronary sinus ring electrode (CSRE) 27, and the coronary sinus coil electrode (CSCE) 28, respectively. The connection port 200 also includes terminals 148 and 150 for connection to the left atrial passive sensing electrodes (LASE) 128 and 130 and terminals 152 and 154 for connection to the left ventricular passive sensing electrodes (LVSE) 132 and 134.

A right ventricular connection port (RV connection port) 220 accommodates the right ventricular lead (RVL) 30 with terminals 52, 54, 56, 58, 144 and 146 that are associated with the right ventricular tip electrode (RVTE) 32, the right ventricular ring electrode (RVRE) 34, the right ventricular coil electrode (RVCE) 36, the SVC coil electrode (SVC CE) 38, and the right ventricular passive sensing electrodes (RVSE) 124 and 126, respectively. A right atrial connection port (RA connection port) 230 accommodates the right atrial lead (RAL) 20 with terminals 42 and 43 that are associated with the right atrial tip electrode (RATE) 22 and the right atrial ring electrode (RARE) 23, respectively, and with terminals 142 and 140 that are associated with right atrial passive sensing electrodes (RASE) 120 and 122.

Thus, switch 74 may selectively connect or disconnect any electrode to function as a cathode or anode during sensing or stimulation by connecting or disconnecting the terminal associated with a particular electrode. In a preferred embodiment, the passive sensing electrodes 120, 122, 124, 126, 128, 130, 132, and 134 are used exclusively for sensing and are therefore only connected to atrial, ventricular, or vector sensing circuits 82, 83, and 84 via switch 74. All other tip, ring or coil electrodes 22, 23, 25, 26, 27, 28, 32, 34, 36 and 38 shown in this embodiment are preferably used exclusively for delivering stimulation and are therefore only connected to atrial or ventricular pulse generators 70 or 72 or shocking circuit 116 as needed for delivering stimulation therapy to a targeted heart chamber.

Figure 4:
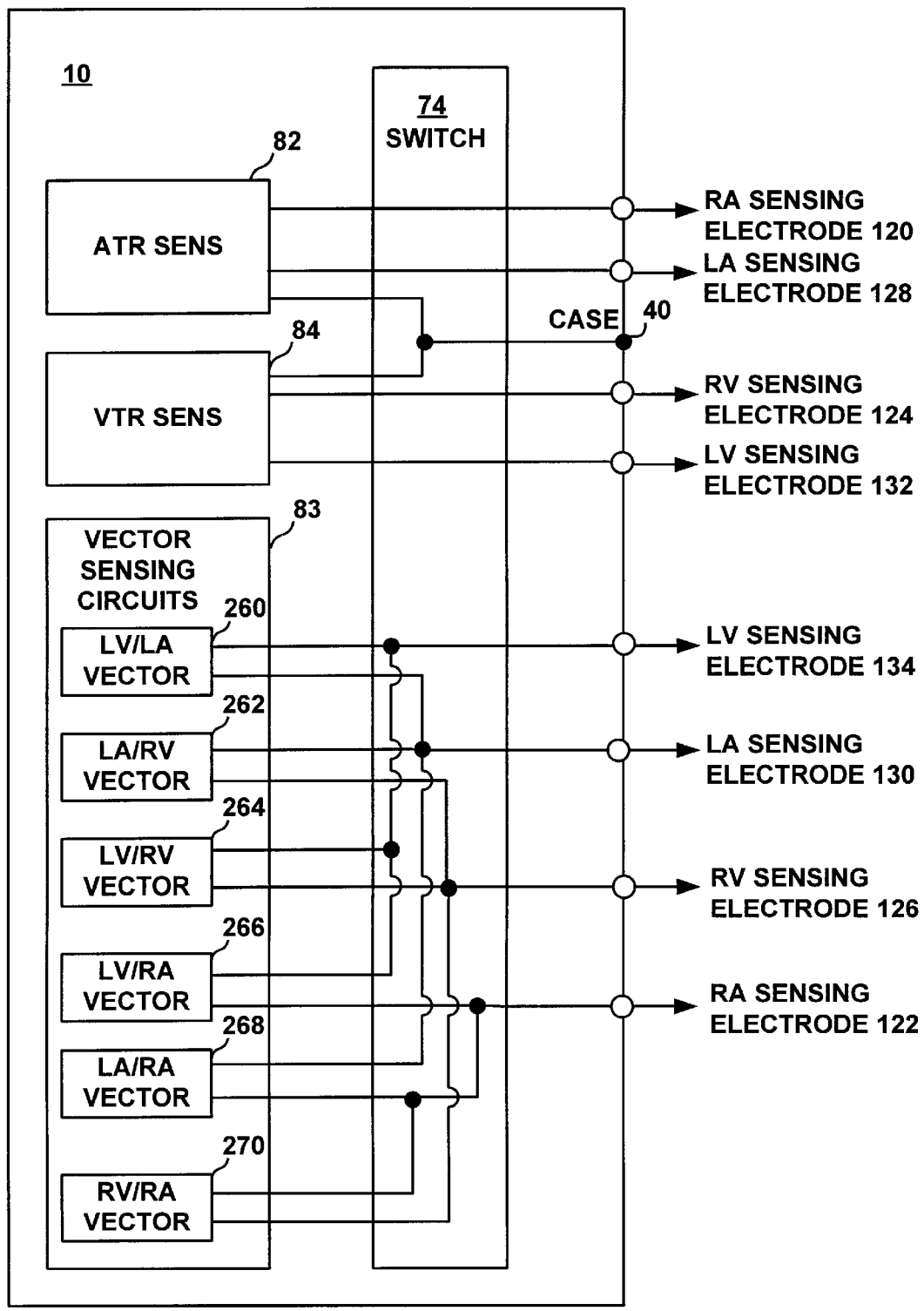
FIG. 4 is a block diagram illustrating the electrical connections within the switch of FIG. 3 for receiving multiple sensing vector signals from passive sensing electrodes positioned in each chamber of the heart.

FIG. 4 illustrates one possible sensing configuration using passive sensing electrodes 120, 122, 124, 126, 128, 130, 132, and 134 to achieve sensing in each of the four heart chambers in addition to sensing vectors directed between each pair of the four heart chambers. Switch 74 connects one passive sensing electrode positioned in each heart chamber to the appropriate atrial sensing circuit 82 or ventricular sensing circuit 84 to obtain the intra-chamber signal from each heart chamber. Thus, right atrial passive sensing electrode 120 and left atrial passive sensing electrode 128 are connected to atrial sensing circuit 82. In the configuration shown in FIG. 4, the case electrode 40 is also connected to the atrial sensing circuit 82 and provides the return electrode such that a unipolar right atrial signal and a unipolar left atrial signal are received. Right ventricular passive sensing electrode 124 and left ventricular passive sensing electrode 132 are connected to ventricular sensing circuit 84, also in a unipolar configuration with the case electrode 40 for sensing of the unipolar right ventricular and unipolar left ventricular signals.

The second passive electrode provided in each heart chamber may then be used in combination with a second passive electrode in any of the other heart chambers to create an inter-chamber sensing vector. Switch 74 connects left ventricular passive sensing electrode 134 to vector sensing circuit 83 with: left atrial passive sensing electrode 130 to receive a left ventricular-to-left atrial sensing vector (LV/LA vector) 260; right ventricular passive sensing electrode 126 to receive a left ventricular-to-right ventricular sensing vector (LV/RV vector) 264; and right atrial passive sensing electrode 122 to obtain a left ventricular-to-right atrial sensing vector (LV/RA vector) 266. Switch 74 further connects left atrial passive electrode 130 to vector sensing circuit 83 with: right atrial passive sensing electrode 122 to receive a left atrial-to-right atrial sensing vector (LA/RA vector) 268; and right ventricular passive sensing electrode 126 to receive a left atrial-to-right ventricular sensing vector (LA/RV vector) 262. The right ventricular passive sensing electrode 126 is connected to vector sensing circuit 83 with right atrial passive sensing electrode 120 to receive a right ventricular-to-right atrial sensing vector (RV/RA vector) 270. Thus, a sensing vector is established across each pair of heart chambers and received by vector sensing circuits 83.

For the sake of illustration, two passive sensing electrodes have been shown in each of the four heart chambers. In alternative embodiments, one or more passive sensing electrodes may be provided in any or all heart chambers. These passive sensing electrodes may then be used in a variety of configurations for sensing intra-chamber or inter-chamber cardiac signals according to individual patient need.

Figure 5:
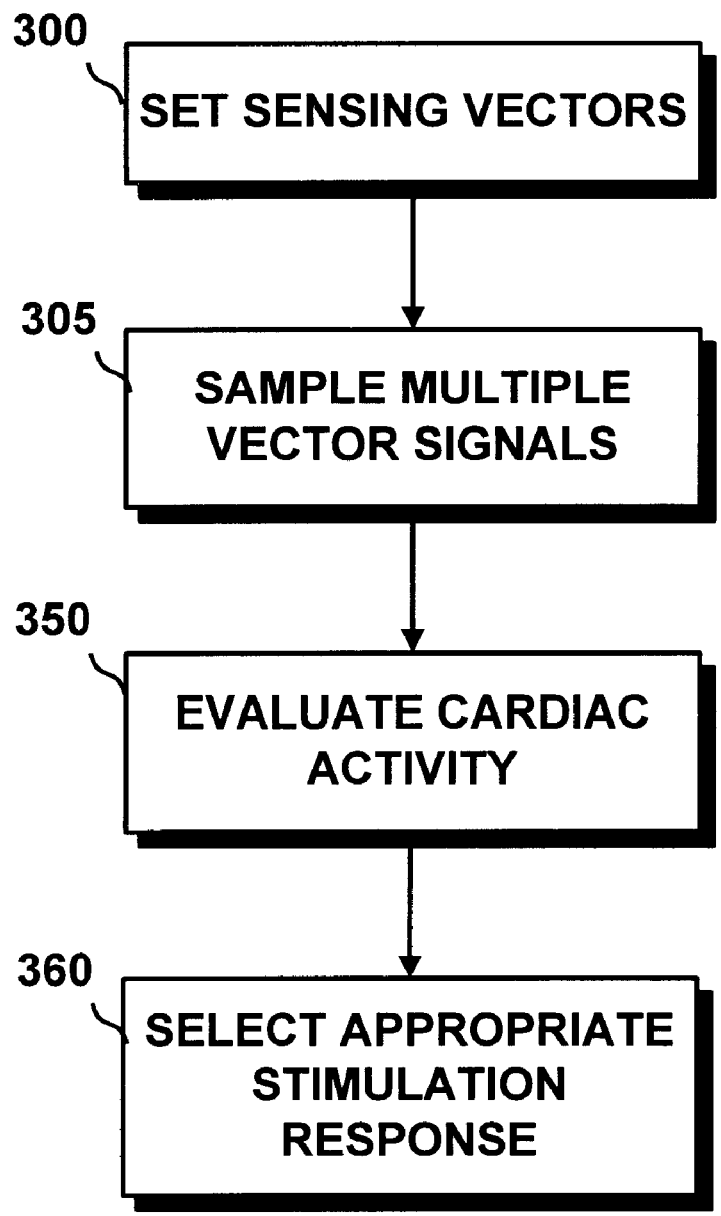
FIG. 5 is a flow chart providing an overview of the operations included in one embodiment of the present invention for sensing multiple sensing vectors in the device of FIG. 2.

In FIG. 5, a flow chart is shown describing an overview of the operation and novel features implemented in one embodiment of the device 10 for precisely evaluating cardiac activity and providing multi-chamber stimulation therapy based upon cardiac events or changes in a heart rhythm detected by receiving sensing vector signals using the passive sensing electrodes 120, 122, 124, 126, 128, 130, 132, and 134. In this flow chart, and the other flow chart presented herein, the various algorithmic steps are summarized in individual "blocks". Such blocks describe specific actions or decisions that must be made or carried out as the algorithm proceeds. Where a microcontroller (or equivalent) is employed, the flow charts presented herein provides the basis for a "control program" that may be used by such a microcontroller (or equivalent) to effectuate the desired control of the stimulation device. Those skilled in the art may readily write such a control program based on the flow charts and other descriptions presented herein.

At step 300, the microcontroller 60 signals switch 74 via control signal 80 to connect the passive sensing electrodes 120, 122, 124, 126, 128, 130, 132, and 134 to atrial sense circuits 82, ventricular sense circuits 84 and vector sense circuits 83 according to a predetermined sensing configuration for acquiring intrachamber and inter-chamber sensing vectors. The sensing vectors to be received, and thus the required sensing configuration, are preferably programmable. For example, the sensing configuration illustrated in FIG. 4 may be used.

At step 305, the intrachamber and inter-chamber signal vectors are sampled. The sampled signal vectors are evaluated at step 350 such that cardiac events may be accurately detected and various time intervals may be measured. Methods that included in the evaluation of cardiac activity at step 350 will be more fully described in conjunction with FIG. 6.

Based upon the information obtained from step 350, the microprocessor 60 determines, at step 360, the appropriate stimulation response to the detected cardiac activity. An appropriate response may include inhibiting stimulation output to one or more chambers, and/or delivering stimulation output to one or more chambers at predefined stimulation output settings and intervals. An appropriate response may also include anti-tachycardia pacing or shocking therapies.

Thus, the present invention enables immediate therapeutic intervention to a measured change in cardiac activity that may be a recognized change in heart failure condition, conduction time, or any other change in a normally sensed rhythm. A measured change may indicate either a progression or an improvement in heart failure condition, and the device 10 may be programmed to respond accordingly.

Figure 6:
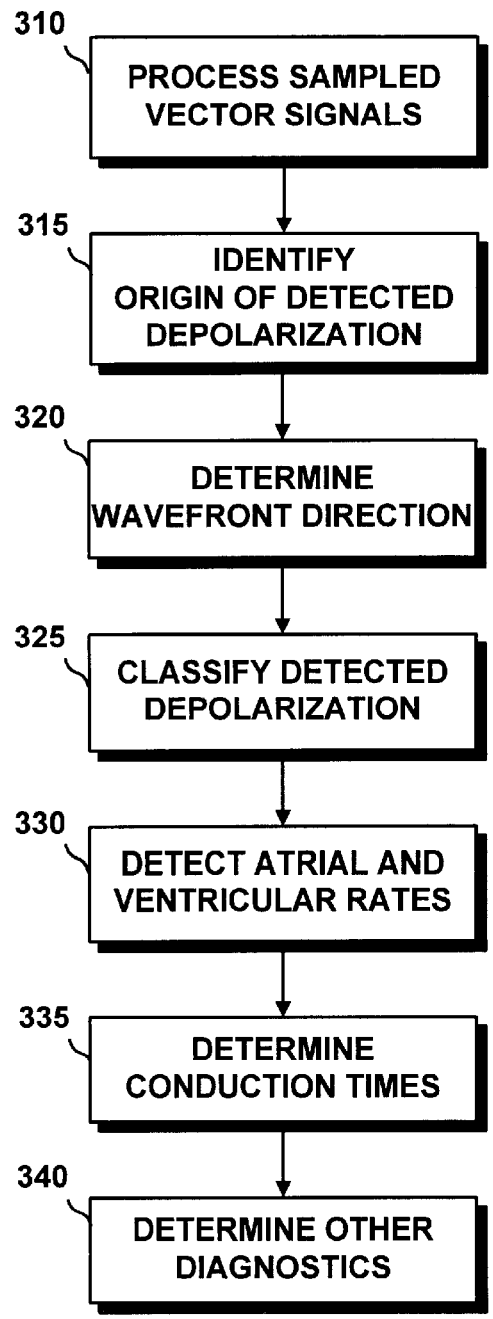
FIG. 6 is a flow chart depicting operation included in one embodiment for evaluating cardiac activity.

The flow chart shown in FIG. 6 illustrates the steps that are included in one embodiment of the present invention for precisely evaluating cardiac activity during the operations of step 350 shown in FIG. 5. At step 310, processing of the sampled vector signals is performed such that cardiac depolarization signals may be detected. Such signal processing may include adding or subtracting sampled vector signals for rejecting noise or eliminating unwanted cross-talk or far-field signals. Cardiac depolarization signals may then be detected from processed vector signals using known threshold detection methods or template morphology matching.

At step 315, the origin of a detected depolarization signal is identified by determining at which sensing site, or in which heart chamber, the depolarization was detected earliest. For example, a detected P-wave is determined to have originated in either the right or the left atrium through comparison of the sampled vector signals.

The direction in which a depolarization wavefront is conducted may also be determined, at step 320, through the comparison of multiple vector signals. The origin of a depolarization signal and the direction in which it is propagated may be used to discriminate sinus P-waves and R-waves from non-sinus events such as retrograde conduction or ectopic beats.

Thus, at step 325, a detected depolarization may be accurately classified according to the type of cardiac event it is, such as a sinus P-wave, sinus R-wave, premature atrial or premature ventricular contraction, retrograde conduction, and so on. Based on this classification, a detected depolarization may be accepted or rejected for use in determining an atrial or ventricular rate, various timing intervals or other diagnostic measures in subsequent steps.

Having determined exactly the origin and type of depolarization detected, accurate determination of atrial and ventricular rates is possible at step 330. Detection of bradycardia, tachycardia or fibrillation is readily determined by measuring the time intervals between confirmed P-waves or confirmed R-waves. Furthermore, accurate discrimination of supraventricular tachycardia and ventricular tachycardia is made possible.

Sampled vector signals may be further analyzed at step 335 to determine the time required for a depolarization wavefront to be conducted through the heart. For example, the time between a P-wave detected first in the right atrium and second in the left atrium may be determined and used as a measure of the intra-atrial conduction time. Likewise, the interval between a detected P-wave or R-wave may be determined as a measure of atrial-ventricular conduction time, and the time between an R-wave detected first in a right ventricle and second in a left ventricle may be measured as the intra-ventricular conduction time. In this way, changes in conduction time of the heart tissue may be recognized, which may indicate a change in clinical condition and further indicate a need for stimulation therapy.

At step 340, other diagnostic measures may be determined, such as the duration of a detected P-wave or R-wave, for the purposes of monitoring changes in heart failure condition. These and other diagnostic indicators that might normally be determined from a 12-lead ECG study performed during an office visit using skin surface electrodes may now be determined automatically through analysis of the multiple sensing vectors provided by the present invention. Device 10 may then respond immediately to a recognized change in heart failure condition by providing or withholding a therapeutic intervention.

Thus, a method and apparatus have been described for precisely evaluating activity in multiple heart chambers using sensing vectors for accurately detecting a cardiac depolarization, determining the origin of a depolarization, determining changes in depolarization conduction time, and determining diagnostic indicators or changes in heart failure condition such that immediate therapeutic intervention may be taken. While detailed descriptions of specific embodiments of the present invention have been provided, it would be apparent to those reasonably skilled in the art that numerous variations of receiving and analyzing sensing vector cardiac signals are possible in which the concepts and methods of the present invention may readily be applied. The descriptions provided herein, therefore, are for the sake of illustration and are not intended to be exclusive.

What is claimed is:

1. A method of accurately detecting cardiac events, for use in a multi-chamber cardiac stimulation device, comprising the steps of:

sensing cardiac signals from passive sensing electrodes placed in at least three cardiac chambers;

establishing a plurality of sensing vectors from the cardiac signals;

detecting a cardiac depolarization from the sensing vectors by comparing a sensing vector to a detection threshold; and selectively delivering a stimulation energy based on a detected cardiac depolarization indicative of a change in a heart function parameter.

2. The method of claim 1, wherein the step of selectively delivering the stimulation energy includes delivering stimulation energy upon any one of a detected change a heart rhythm or a heart failure condition.

3. The method of claim 1, wherein the step of establishing the sensing vectors includes establishing intra-chamber sensing vectors.

4. The method of claim 3, wherein the step of establishing the sensing vectors further includes establishing inter-chamber sensing vectors.

5. The method of claim 4, wherein the step of detecting the cardiac depolarization includes sampling the vector signals to identify an origin and a direction of propagation of the cardiac depolarization.

6. The method of claim 5, wherein the step of detecting the cardiac depolarization includes comparing a vector signal to a predetermined signal morphology template.

7. The method of claim 5, further including the step of classifying the detected depolarization.

8. The method of claim 5, wherein the classifying step includes classifying the detected depolarization according to the identified origin.

9. The method of claim 5, wherein the classifying step includes classifying the detected depolarization according to the identified direction of conduction.

10. The method of claim 4, wherein the step of establishing the sensing vectors includes establishing a vector between a right atrium and a left atrium.

11. The method of claim 4, wherein the step of establishing the sensing vectors includes establishing a vector between a right atrium and a right ventricle.

12. The method of claim 4, wherein the step of establishing the sensing vectors includes establishing a vector between a right atrium and a left ventricle.

13. The method of claim 4, wherein the step of establishing the sensing vectors includes establishing a vector between a left atrium and a right ventricle.

14. The method of claim 4, wherein the step of establishing the sensing vectors includes establishing a vector between a left atrium and a left ventricle.

15. The method of claim 4, wherein the step of establishing the sensing vectors includes establishing a vector between a right ventricle and a left ventricle.

16. The method of claim 4, wherein the step of establishing the sensing vectors includes adding two or more cardiac signals.

17. The method of claim 4, wherein the step of establishing the sensing vectors includes subtracting two or more cardiac signals.

18. The method of claim 1, wherein the step of establishing the sensing vectors further includes establishing inter-chamber sensing vectors.

19. The method of claim 1, further including the step of detecting a heart rate by determining a time interval between a first detected depolarization and a second detected depolarization.

20. The method of claim 19, wherein the step of selectively delivering the stimulation energy includes delivering stimulation energy in response to a heart rate determined to be pathologic.

21. The method of claim 20, wherein the step of selectively delivering the stimulation energy includes delivering a stimulation pulse to a heart chamber at a predetermined time interval following a detected cardiac depolarization.

22. The method of claim 20, wherein the step of selectively delivering the stimulation energy includes withholding stimulation.

23. The method of claim 1, further including the step of measuring a conduction time as a time interval between a first detected depolarization and a second detected depolarization.

24. The method of claim 23, wherein the step of selectively delivering the stimulation energy includes delivering stimulation energy in response to a change in the conduction time.

25. The method of claim 1, further including the step of determining a diagnostic parameter as an indication of heart function.

26. The method of claim 25, wherein the step of determining the diagnostic parameter includes determining a duration of a depolarization signal.

27. A multi-chamber cardiac stimulation device that accurately detects cardiac events, comprising:

passive sensing electrodes placed in at least three cardiac chambers;

sensing circuits, connected to the sensing electrodes, that sense cardiac signals;

control circuit that establishes a plurality of sensing vectors from the cardiac signals, and that detects a cardiac depolarization from the sensing vectors by comparing a sensing vector to a detection threshold; and a pulse generator that selectively delivers a stimulation energy based on a detected cardiac depolarization indicative of a change in a heart function parameter.

28. The device of claim 27, wherein the pulse generator delivers stimulation energy upon any one of a detected change a heart rhythm or a heart failure condition.

29. The device of claim 27, wherein the sensing vectors include intra-chamber sensing vectors.

30. The device of claim 29, wherein the sensing vectors further include inter-chamber sensing vectors.

31. The device of claim 27, wherein the detected cardiac depolarization includes an origin and a direction of propagation.

32. The device of claim 27, wherein the sensing vectors include any one or more of the following:

a vector between a right atrium and a left atrium;

a vector between a right atrium and a right ventricle;

a vector between a right atrium and a left ventricle;

a vector between a left atrium and a right ventricle;

a vector between a left atrium and a left ventricle; and a vector between a right ventricle and a left ventricle.

33. The device of claim 27, wherein the pulse generator delivers the stimulation energy to a heart chamber at a predetermined time interval following the detected cardiac depolarization.

34. A multi-chamber cardiac stimulation device that accurately detects cardiac events, comprising:

means for passively sensing cardiac signals;

means for establishing a plurality of sensing vectors from the cardiac signals;

means for detecting a cardiac depolarization from the sensing vectors by comparing a sensing vector to a detection threshold; and means for selectively delivering a stimulation energy based on a detected cardiac depolarization indicative of a change in a heart function parameter.

35. The device of claim 34, wherein the heart function parameter includes any one of a detected change a heart rhythm or a heart failure condition.

36. The device of claim 34, wherein the sensing vectors include intra-chamber sensing vectors.

37. The device of claim 36, wherein the sensing vectors further include inter-chamber sensing vectors.

38. The device of claim 34, wherein the detected cardiac depolarization includes an origin and a direction of propagation.

39. The device of claim 34, wherein the sensing vectors include any one or more of the following:

a vector between a right atrium and a left atrium;

a vector between a right atrium and a right ventricle;

a vector between a right atrium and a left ventricle;

a vector between a left atrium and a right ventricle;

a vector between a left atrium and a left ventricle; and a vector between a right ventricle and a left ventricle.

40. The device of claim 34, wherein the pulse generator delivers the stimulation energy in response to a change in the conduction time at a predetermined time interval following the detected cardiac depolarization.

* * * * *